United States Patent [19]

Nudelman et al.

[11] 4,150,224
[45] * Apr. 17, 1979

[54] 7[[(1-PYRROLLYL)7 ACETYL]AMINO]CEPHALOSPORIN DERIVATIVES

[75] Inventors: Abraham Nudelman, Rehovot; Abraham Patchornik, Ness Ziona, both of Israel

[73] Assignee: Yeda Research and Development Co., Ltd., Rehovot, Israel

[ * ] Notice: The portion of the term of this patent subsequent to Apr. 10, 1996, has been disclaimed.

[21] Appl. No.: 839,164

[22] Filed: Oct. 4, 1977

[51] Int. Cl.[2] .............................................. C07D 501/36
[52] U.S. Cl. .......................................... 544/27; 544/21; 544/28; 260/326.43
[58] Field of Search .................................... 544/27, 21

[56] References Cited

U.S. PATENT DOCUMENTS 3,929,779  12/1975  Bickel et al. ............................. 544/27
3,971,780   7/1976  Cimarusti et al. ....................... 544/27

Primary Examiner—Donald G. Daus
Assistant Examiner—David E. Wheeler
Attorney, Agent, or Firm—L. Ruth Hattan; Eugene O. Retter; George W. Rauchfuss, Jr.

[57] ABSTRACT

Novel cephalosporin compounds useful as antibiotics having the following formula and pharmaceutically useful salts thereof:

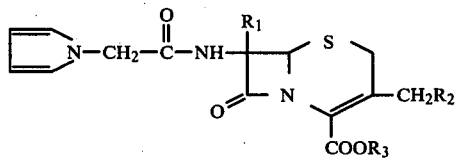

6 Claims, No Drawings

7[[(1-PYRROLLYL)7 ACETYL]AMINO]CEPHALOSPORIN DERIVATIVES

BACKGROUND OF THE INVENTION

1. Field of the Invention

This invention is directed to new pyrrole cephalosporin derivatives, useful as antibiotics, and methods of preparation of said cephalosporin derivatives.

2. Description of the Prior Art

U.S. Pat. No. 3,218,318 describes a variety of heteromonocyclic derivatives of 7-aminocephalosporanic acid. In particular

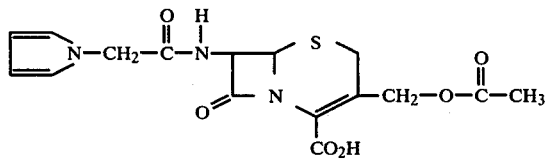

the (1-pyrryl)acetyl derivative of 7-aminocephalosporanic acid, shown above, is described and claimed in the above identified patent. U.S. Pat. Nos. 3,351,596, 3,459,746 and 3,252,973 disclose the use of (1-pyrryl)acetic acid in the preparation of cephalosporin and/or pencillin derivatives. U.S. Pat. No. 3,728,342; U.S. Pat. No. 3,799,924; E. Ger. 109,638; W. Ger. Offen No. 2,262,477 and Belgium Pat. No. 768,653 disclose cepholosporin and/or pencillin derivatives which may contain an N-pyrryl group. U.S. Pat. No. 3,536,698 indicates that (1-pyrryl)acetic acid derivatives of 6-aminopenicillin acid and 7-aminocephalosporanic acid are useful as intermediates in the formation of alkyl, haloalkyl, phenyl or benzyl esters.

None of these references describe or suggest the compounds claimed in this invention.

SUMMARY OF THE INVENTION

Compounds of formula 1 are useful as antibiotics

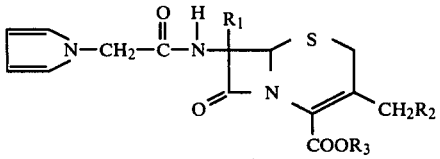

Formula 1 wherein $R_1$ is hydrogen or methoxy, $R_2$ is 1,3,4-thiadiazol-2-ylthio, 5-methyl-1,3,4-thiadiazol-2-ylthio, tetrazol-5-ylthio, 1-methyltetrazol-5-ylthio, 1,3,4-oxadiazol-2-ylthio, 5-methyl-1,3,4-oxadiazol-2-ylthio, 1,3,4-triazol-2-ylthio, 1,2,3-triazol-5-ylthio; $R_3$ is hydrogen, a pharmaceutically acceptable cation of an alkali metal or an alkaline earth metal, ammonium, or organic ammonium cations, a straight or branched alkyl group of from 1 to 4 carbon atoms, an alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched alkyl group of from 1 to 4 carbon atoms, p (alkanoyloxy)benzyl group in which the alkanoyl moiety is straight or branched and has from 2 to 5 carbon atoms, an aminoalkanoyloxymethyl group in which the alkanoyl moiety has from 2 to 15 carbon atoms and the amino nitrogen may be mono- or di-substituted with a straight or branched alkyl group having from 1 to 4 carbon atoms.

DETAILED DESCRIPTION

In formula 1 the substituent group represented by $R_3$ in addition to being hydrogen or a cation may be a straight or branched alkyl group of from 1 to 4 carbon atoms; an alkanoyloxymethyl group as represented by the structure

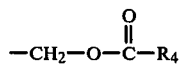

wherein $R_4$ is selected from a straight or branched alkyl group of from 1 to 4 carbon atoms; an alkanoylaminomethyl group or an alkoxycarbonylaminomethyl group as represented by the structure

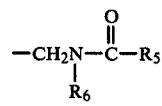

wherein $R_5$ is a straight or branched alkyl group of from 1 to 4 carbon atoms or a straight or branched alkoxy group of from 1 to 4 carbon atoms, and $R_6$ is selected from hydrogen and an alkyl group of from 1 to 4 carbon atoms; a p-(alkanoyloxy)benzyl group as represented by the structure

wherein $R_7$ is a straight or branched alkyl group of from 1 to 4 carbon atoms; and an aminoalkanoyloxymethyl group as represented by the group

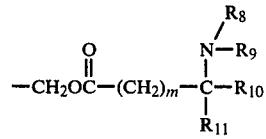

wherein m is 0 to 5, each of $R_8$ and $R_9$ is selected from hydrogen or an alkyl group of from 1 to 4 carbon atoms, and each of $R_{10}$ and $R_{11}$ is selected from hydrogen or a straight or branched alkyl group of from 1 to 4 carbon atoms.

Illustrative examples of straight or branched alkyl groups of from 1 to 4 carbon atoms which $R_4$, $R_5$, $R_6$, $R_7$, $R_8$, $R_9$, $R_{10}$, and $R_{11}$ may represent are methyl, ethyl, n-propyl, isopropyl, n-butyl, iso-butyl and tert-butyl.

The pharmaceutically acceptable cations which may be present as the group $R_3$ in the compounds of formula 1 include alkali metal and alkaline earth metal ions, for example, sodium ion, potassium ion, magnesium ion, calcium ion as well as ammonium, an organic amine cation, selected from a primary, a secondary, a tertiary amine cation and a quaternary ammonium cation for example, triethylammonium, methylammonium, dibutylammonium and N-ethyl piperidinium ion. These salt forms may be prepared in the manner recognized in the art and may be formed in situ or by reacting the corresponding acid with base, for example, sodium bicarbonate or triethylamine.

In formula 1, the substituent group $R_2$ represents a heterocyclicthio group selected from 1,3,4-thiadiazol-2-ylthio, 5-methyl-1,3,4-thiadiazol-2-ylthio, tetrazol-5-ylthio, 1-methyltetrazol-5-ylthio, 5-methyl-1,3,4-oxadiazol-2-ylthio, 1,3,4-oxadiazol-2-ylthio, 1,2,3-triazol-5-ylthio, 1,3,4-triazol-2-ylthio, 5-methyl-1,3,4-triazol-2-ylthio as represented by the following respective structures:

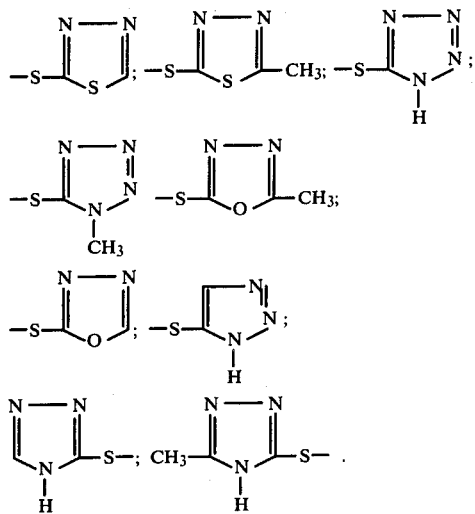

In formula 1, $R_1$ may be hydrogen or methoxy, hydrogen being preferred, and $R_1$ may be either cis or trans to the hydrogen at position 6. The preferred orientation occurs when $R_1$ is cis to the hydrogen at position 6.

The preferred compounds of this invention are compounds as represented by formula 1 wherein $R_1$ is hydrogen, $R_2$ is 1-methyltetrazol-5-ylthio or 5-methyl-1,3,4-thiadiazol-2-ylthio and $R_3$ is hydrogen or pharmaceutically acceptable salts thereof.

The non-toxic inorganic acid addition salts of the compounds of this invention such as mineral acid addition salts, for example, hydrogen chloride, hydrogen bromide, hydrogen iodide, sulfates, sulfamate, phosphate, and organic acid addition salts, for example, maleate, acetate, citrate, oxalate, succinate, benzoate, tartrate, fumarate, malate, mandelate, and ascorbate, are also included within the scope of this invention.

The compounds of this invention may be administered in a manner similar to that of many well-known cephalosporin compounds, for example, cephalexin, cephalothin, or cephaloglycine. They may be administered alone or in the form of pharmaceutical preparations either orally or parenterally and topically to warm blooded animals, that is, birds, and mammals, for example, cats, dogs, cows, sheep and horses, and humans. For oral administration, the compounds may be administered in the form of tablets, capsules or pills or in the form of elixirs or suspensions. For parenteral administration, they may best be used in the form of a sterile aqueous solution which may contain other solutes, for example, enough saline or glucose to make the solution isotonic. For topical administration, the compounds may be incorporated in creams or ointments.

Illustrative examples of bacteria against which the compounds of this invention are active are: *Streptococcus pneumoniae, Staphylococcus aureus, Salmonella schottmuelleri, Escherichia coli, Klebsiella pneumoniae* and *Proteus mirabilis.*

An illustrative example of this invention is 7[[(1-pyrryl)acetyl]amino]-3-[[(1-methyltetrazol-5-yl)thio]methyl]-8-oxo-5-thia-1-azabicyclo[4.2.0]oct-2-ene-2 carboxylic acid. Additional examples of compounds are described hereinafter.

Compounds of this invention are prepared by coupling 1 equivalent of a compound represented by formula 2

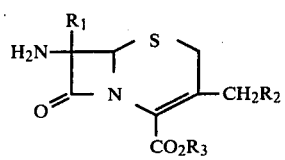

Formula 2 wherein $R_1$, $R_2$ and $R_3$ have the meanings defined in formula 1, with 1 equivalent of the compound of formula 3 or a functional equivalent thereof

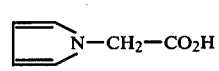

Formula 3 to yield compounds represented by formula 1.

Functional equivalents of the acid as represented by formula 3 include the acid halide (acid chloride), acid anhydride, including mixed anhydrides with, for example, alkylphosphoric acids, lower aliphatic mono esters of carbonic acid or alkyl or aryl sulfonic acids.

The coupling reaction is generally carried out in the presence of a solvent. Suitable solvents include ethyl acetate, acetone, dioxane, acetonitrile, chloroform, ethylene chloride, tetrahydrofuran, dimethylformamide, benzene or benzene-ethanol. As hydrophilic solvents are employed, mixtures of these solvents with water are also suitable for the above reactions. The coupling reaction is generally carried out in the presence of a base, for example, an alkaline bicarbonate or an amine. The temperature of the reaction may vary from −10° to 100° C., and the reaction time may vary from about ½ hour to 10 hours. The cephalosporin products are isolated by conventional methods.

An carbodiimide, coupling reaction is represented by the coupling of an acid as represented by a compound of formula 3 with an amine as represented by a compound of formula 2 using a carbiimide, for example, N,N'-diisopropylcarbodiimide or N,N-dicyclohexylcarbodiimide. The general procedure is described in U.S. Pat. No. 3,252,973.

A second illustrative coupling reaction is the mixed anhydride method as described by Spencer, et al., *J. Med. Chem.*, 9, 746 (1966). The acid, represented by compounds of formula 3 to be coupled is reacted with an alkylchloroformate, for example, iso-butylchloroformate, at about −10° C. in a solvent which contains an acid acceptor such as triethylamine. The amine, represented by a compound of formula 2, with which the acid is to be coupled is added, and the temperature is increased from about −10° C. to room temperature (about 20° C.). The coupled product is recovered by conventional techniques.

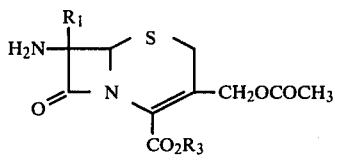

Formula 4

Compounds of formula 4 wherein $R_1$ is hydrogen, and $R_3$ is hydrogen or a cation are commercially available or may be prepared by methods well-known in the art. The corresponding compounds wherein $R_1$ is methoxy and $R_3$ is hydrogen may be prepared by the general procedures described in U.S. Pat. No. 3,778,432.

Compounds of formulas 1 and 2 wherein $R_3$ is alkanoyloxymethyl may be prepared by reacting the corresponding acid in the form of a salt, such as an alkali metal salt or the triethylammonium salt with a compound of formula

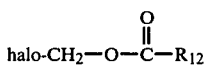

wherein halo is chlorine or bromine, and $R_{12}$ is a straight or branched alkyl group of form 1 to 4 carbon atoms, by the general procedure described in U.S. Pat. No. 3,655,658.

Compounds of formulas 1 and 2 wherein $R_3$ is alkanoylaminomethyl or alkoxycarbonylaminomethyl are prepared by treating the sodium salt of acid derivatives of formula 2 in an organic solvent such as dimethylformamide or hexamethylphosphoramide, at room temperature with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of formulas 1 and 2 wherein $R_3$ is p-(alkanoyloxy)benzyl are prepared by adding two equivalents of the p-(alkanoyloxy)benzyl alcohol to a suspension of sodium salt of acid derivatives of formula 2 and dimethylformamide or hexamethylphosphoramide after which the mixture is cooled to 0° C. 1.2 equivalents of dicyclohexylcarbodiimide in dimethylformamide are added dropwise to the mixture with stirring. The mixture is stirred at 0° C. for ½ to 3 hours and then an additional 2 to 5 hours at room temperature. The formed dicyclohexylurea is removed by filtration and the filtrate is diluted with chloroform, methylene chloride or ethylacetate, washed with water and dried to give the product.

Compounds of formulas 1 and 2 wherein $R_3$ is aminoalkanoyloxymethyl are prepared by mixing a suspension of the sodium salt of an acid of formula 2 and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride washed with water, aqueous base, then water. The organic phase is separated and the precipitate isolated by conventional means followed by deprotection of the amine group to give the product.

Compounds of formulas 1 and 2 wherein $R_3$ is a straight or branched 1 to 4 carbon alkyl group are prepared by mixing a suspension of the sodium salt of an acid of formula 2 with an excess of an appropriate alkyl halide, usually alkylchloride or alkyl bromide, in a solvent such as dimethylformamide or hexamethylphosphoramide for from 2 to 24 hours. The mixture is diluted with a solvent such as ethyl acetate or methylene chloride, washed with water, aqueous base and water. The organic phase is removed and the ester is recovered by conventional methods. Although the tert-butyl ester may be prepared by this method, it is preferred to use the method described in *J. Med. Chem.*, 9, 444 (1966). The appropriate cephalosporin derivative, for example, 3-[(acetyloxy)methyl]-7-amino-8-oxo-5-thia-1-azabicyclo[4.2.0]oct-2-ene-2-carboxylic acid is added to dioxane containing sulfuric acid and liquid isobutylene in a pressure bottle. The mixture is reacted overnight at room temperature. The tert-butyl ester of 3-[(acetyloxy)methyl]-7-amino-8-oxo-5-thia-1-azabicyclo[4.2.0]oct-2-ene-2-carboxylic acid is recovered from the reaction mixture.

Compounds of formula 2 wherein $R_1$ is hydrogen or methoxy, $R_3$ is hydrogen and $R_2$ is a heterocyclic thio group selected from 1,3,4-thiadiazol-2-ylthio, 5-methyl-1,3,4-thiadiazol-2-ylthio, tetrazol-5-ylthio, 1-methyl-tetrazol-5-ylthio, 1,3,4-oxadiazol-2-ylthio, 5-methyl-1,3,4-oxadiazol-2-ylthio, 1,3,4-triazol-2-ylthio, 5-methyl-1,3,4-triazol-2-ylthio, 1,2,3-triazol-5-ylthio; are prepared by dissolving 1 equivalent of the acid as represented by the formula 4 ($R_1$ is hydrogen or methoxy) in the form of a salt, such as the sodium salt in about 500 to 2000 ml of water at a temperature of from 30° to 90° C. under a nitrogen atmosphere and subsequently adding 1 equivalent of a base, such as triethylamine or sodium bicarbonate and 1 to 3 equivalents of an appropriate heterocyclic thio group defined above for $R_2$. The reaction mixture is stirred at 30° to 90° C. for about 2 to 6 hours after which the water is evaporated, and the residue is taken up in an organic solvent, such as, methanol, ethanoll, or dimethylformamide, and precipitated with an organic solvent, such as, acetonitrile, acetone, ethyl acetate or chloroform.

In a similar manner, compounds as represented by formula 1 may be prepared by reacting compounds as represented by formula 5

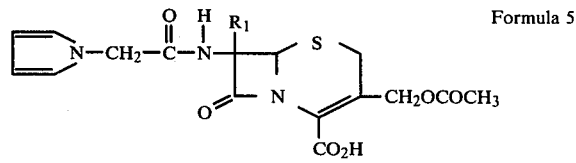

Formula 5 with a heterocyclicthiol compound represented by $R_2$ as defined in formula 1. This is an alternate method to prepare the compounds of this invention.

The acid, as represented by formula 3, is prepared according to the method of Gloede, et al., Collect. Czech. Chem. Commun., 33, 1307 (1968). Glycine or an ester of glycine, for example, the methyl or ethyl ester, is reacted with a 2,5-dialkoxytetrahydrofuran (the alkoxy groups are straight or branched and have from 1 to 4 carbon atoms) in refluxing acetic acid which may contain sodium acetate. Conventional work-up methods are employed in isolating the acid represented by formula 3.

The method of Clemo, et al., J. Chem. Soc., 49 (1931), may also be used to prepare the acid of formula 3.

It has been observed that 7-[[(1-pyrryl)acetyl]-amino]-3[[(1-methyltetrazol-5-yl)thio]methyl]-8-oxo-5-thia-1-azabicyclo[4.2.0]oct-2-ene-2-carboxylic acid, a 3-sulfur hetero cephalosporin, is superior to 3-[(acetyloxy)methyl]-7-[[(1-pyrryl)acetyl]amino]-8-oxo-5-thia-1-azabicyclo[4.2.0] oct-2-ene-2-carboxylic acid when tested in vitro against various bacteria.

A typical parenteral solution may have the following composition.

| 7-[[(1-pyrryl)acetyl]amino]-3-[[1-methyl-tetrazol-5-yl)thio]methyl]-8-oxo-5-thia-1-azabicyclo[4.2.0]oct-2-ene-2-carboxylic acid, sodium salt | 1.0 g |
|---|---|
| White beeswax | 1.0 g |
| Peanut oil, to make | 10.0 cc |

Melt wax into a portion of the peanut oil. Add the remainder of the oil. Sterilize the oil-wax mixture at 150° C. with dry heat for 2 hours. Under sterile conditions mix the cephalosporin into the wax-oil mixture and place in a 25 cc ampule previously sterilized and seal ampul. For use, dilute with 10 cc of pure water; each cc contains 50 mg of cephalosporin.

A typical ointment can have the following composition.

| 7-[[(1-pyrryl)acetyl]amino]-3-[[(1-methyl-tetrazol-5-yl)thio]methyl]-8-oxo-5-thia-1-azabicyclo[4.2.0]oct-2-ene-2-carboxylic acid, sodium salt | 50 mg/gram of ointment |
|---|---|
| Hydrophilic Base | |
| Cetyl alcohol | 15% |
| White Wax | 1% |
| Sodium Lauryl sulfate | 2% |
| Propylene glycol | 10% |
| Water | 72% |

Add the cephalosporin derivative to a small amount of water and incorporate into the base.

EXAMPLE 1

3-(Acetyloxy)methyl-7-amino-8-oxo-5-thia-1-azabicyclo [4.2.0]oct-2-ene-2-carboxylic acid tert-butyl ester 3-(Acetyloxy)methyl-7-amino-8-oxo-5-thia-1-azabicyclo[4.2.0]oct-2-ene-2-carboxylic acid (0.04 mole) is added to 100 ml of dioxane, 10 ml of concentrated sulfuric acid and 50 ml of liquid isobutylene in a pressure bottle. The mixture is shaken overnight. The bottle is chilled, opened and the contents poured into ice cold solution of sodium bicarbonate. Extraction of the aqueous phase with ethyl acetate followed by drying and evaporation of the ethyl acetate phase gives the tert-butyl ester, m.p. 111°–112° C. See J. Med. Chem., 9, 444 (1966).

In like manner using sufficient quantities of 7-amino-3-methyl-8-oxo-5-thia-1-azabicyclo[4.2.0]oct-2-ene-2-carboxylic acid and 7-amino-3-[[(5-methyl-1, 3, 4-thiadiazol-2-yl)thio]methyl]-8-oxo-5-thia-1-azabicyclo-[4.2.0]oct-2-ene-2-carboxylic in place of 3-[(acetyloxy)-methyl]-7-amino-8-oxo-5-thia-1-azabicyclo[4.2.0]oct-2-ene-2-carboxylic acid, the corresponding tert-butyl esters are prepared respectively:
7-amino-3-methyl-8-oxo-5-thia-1-azabicyclo[4.2.0]oct-2-ene-2-carboxylic acid tert-butyl ester and
7-amino-3-[[(5-methyl-1, 3, 4-thiadiazol-2-yl)thio]-methyl]-8-oxo-5-thia-1-azabicyclo[4.2.0]oct-2-ene-2-carboxylic acid tert-butyl ester.

EXAMPLE 2

(1-Pyrryl)acetic Acid

To a 1 liter flask fitted with a condenser, a magnetic stirrer and a nitrogen inlet tube is added acetic acid (glacial, 300 ml) and sodium acetate (32.8g; 0.4 mole). The system is purged with nitrogen and a positive nitrogen pressure is maintained. Then glycine (15.0g; 0.2 mole) is added and the solution is heated to reflux. To the refluxing, clear solution is added 2,5-dimethoxytetrahydrofuran (29 ml, 0.2 mole) over a period of 2 - 3 minutes; refluxing is continued an additional 2 minutes. The reaction mixture is cooled in an ice bath and most of the acetic acid is removed under vacuum. The residue is taken up in water and extracted with four portions of ether. The ether extracts are washed with water, dried over anhydrous magnesium sulfate, filtered and the ether is evaporated to yield a slurry. The slurry is taken up into toluene, filtered through celite and crystallized by cooling to give 8.41g. (33.6%) of the title compound. M.P. 88°–90° C.

Substitution of 2,5-diethoxytetrahydrofuran for the 2,5-dimethoxy derivative gives slightly better yeilds. Glycine ethyl ester hydrochloride, used in place of glycine, gives comparable results.

EXAMPLE 3

7-[[2-(1-Pyrryl)acetyl]amino]-3-[[1-methyltetrazol-5-yl)thio]methyl]-8-oxo-5-thia-1-azabicyclo[4.2.0]oct-2-ene-2-carboxylic acid A solution of (1-pyrryl) acetic acid (1.5 g, 0.02 mole) and triethylamine (2.48 ml, 0.02 mole) in 80 ml of tetrahydrofuran is cooled to 0° C. While stirring, isobutyl chloroformate (2.6 ml, 0.02 mole) is added and the temperature maintained at 0° C. for 15 min. A cold solution of 3-[[(1-methyltetrazol-5-yl)thio]methyl]-7-amino-8-oxo-5-thia-1-azabicyclo[4.2.0]oct-2-ene-2-carboxylic acid (6.56 g, 0.02 mole) and triethylamine (2.48 ml, 0.02 mole) in 72 ml of 50% aqueous tetrahydrofuran is added with stirring to the previous solution.

The mixture is stirred at 5° C. for 1 hour and at room temperature for an additional hour. The tetrahydrofuran is evaporated and the residue is dissolved in 100 ml of water and is washed with ethyl acetate. The aqueous phase is covered with a fresh layer of ethyl acetate, cooled in ice and acidified to pH 3 with 6N hydrochloric acid. The mixture is filtered and the ethyl acetate separated. The aqueous phase is washed with fresh ethyl acetate. The combined ethyl acetate fractions are dried over magnesium sulfate, treated with charcoal, filtered, flash concentrated to 10–30 ml and added with vigorous stirring to a mixture of ether hexane. The title compound is recovered a solid in 20% yield.

NMR(DMSO-D6) ppm (δ) 3.73 (broad s,2), 3.98 (s,3), 4.35 (broad s,2), 4.67 (s,2), 5.11 (d,1), 5.72 (d,1) 6.01 (t,1) 6.69 (t,1).

EXAMPLE 4

3-[(Acetyloxy)methyl]-7-[[2-(1-pyrryl)acetyl]amino]-8-oxo-5-thia,1-azabicyclo[4.2.0]oct-2-ene-2-carboxylic acid A solution of (1-pyrryl)acetic acid (2.5 g, 0.02 mole) and triethylamine (2.48 ml, 0.02 mole) in 80 ml of tetrahydrofuran is cooled to 0° C. While stirring, iso-butyl chloroformate (2.6 ml, 0.02 mole) is added and the temperature maintained at 0° C. for 15 min. A cold solution of 3-[(acetyloxy)methyl]-7-amino-8-oxo-5-thia-1- azabicyclo[4.2.0]oct-2-carboxylic acid (5.44 g, 0.02 mole) and triethylamine (2.48 ml, 0.02 mole) in 72 ml of 50% aqueous tetrahydrofuran is added with stirring to the solution containing the mixed anhydride of (1-pyrryl)acetic acid.

The mixture is stirred at 5° C. for 1 hour and at room temperature for an additional hour. The tetrahydrofuran is evaporated and the residue is dissolved in 100 ml of water and is washed with ethyl acetate. The aqueous phase is covered with a fresh layer of ethyl acetate, cooled in ice and acidified to pH 3 with 6N hydrochloric acid. The mixture is filtered and the ethyl acetate separated. The aqueous phase is washed with fresh ethyl acetate. The combined ethyl acetate fractions are dried over magnesium sulfate, treated with charcoal, flash concentrated to 10-30 ml and added with vigorous stirring to a mixture of ether-hexane. The title compound precipitates as a yellow powder 4.0 g (53% yield).

NMR (DMSO-D$_6$+D$_2$O) ppm ($\delta$) 2.0 (s,3), 3.57 (broad s,2), 4.67 (s,2), 4.89 (q,2), 5.13 (d,1), 5.78 (d,1), 6.03 (t,2), 6.72 (t,2).

EXAMPLE 5

7-[[(1-Pyrryl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid (1-Pyrryl)acetic is added to water, the pH of which is adjusted to about 6.5 by the addition of sodium bicarbonate. This solution is cooled in an ice bath and to it is added one equivalent of 3-[[(5 methyl - 1, 3, 4-thiadiazol-2-yl) thio]methyl]-7-amino-8-oxo-5-thia-1-azabicyclo[4.2.0]oct-2-ene-2-carboxylic acid (7-ATDCA) followed by N, N'-dicyclohexylcarbodiimide in cold dioxane. The mole ratio of (1-pyrryl) acetic acid/7-ATDCA/carbodiimide is 3/1/1. After standing overnight at ice bath temperature, the reaction mixture is filtered to remove solids. The filtrate is evaporated to dryness, the solids taken up in ethyl acetate, dried over magnesium sulfate and filtered. The ethyl acetate solution is concentrated and then treated with hexane. The title compound precipitates from solution is filtered and dried.

EXAMPLE 6

7-[[(1-Pyrryl)acetyl]amino]-3-[[(1-methyltetrazol-5-ylthio]methyl-8-oxo-5-thia-2-azabicyclo[4.2.0]oct-2-ene-2-carbocyclic acid 3-[(Acetyloxy)methyl]-7-[[2-(1-pyrryl)acetyl]amino]-8-oxo-5-thia-1-azabicyclo[4.2.0]oct-2-ene-2-carboxylic acid sodium salt, one equivalent, and a molar equivalent of sodium bicarbonate are dissolved in a phosphate buffer, pH=6.4. A slight molar excess of 1-methyltetrazol-5-ylthiol is added and the solution is stirred for about 6 hours at 60° C. The pH is adjusted to about 3 by the addition of hydrochloric acid. Ethyl acetate is used to extract the product. The ethyl acetate solution is washed with saturated sodium chloride solution, dried over magnesium sulfate. Then the ethyl acetate is removed under vacuum below 50° C. and the title compound is recovered.

EXAMPLE 7

7[[(1-Pyrryl)acetyl]amino]-3-[[(1-methyltetrazol-5-yl)thio]methyl]-8-oxo-5-thia-1-azabicyclo[4.2.0]oct-2-ene-2-carboxylic acid pivaloyloxymethyl ester To dimethylformamide is added the sodium salt of 7[[(1-pyrryl)acetyl]amino]-3-[[(1-methyltetrazol-5-yl) thio]methyl]-8-oxo-5-thia-1-azabicyclo[4.2.0]oct-2-ene-2-carboxylic, one equivalent, and the solution is stirred at room temperature for about 30 minutes after which an equivalent of chloromethylpivalate is added. Stirring is continued for about 3 hours. The solution is diluted with ethyl acetate and washed with water. The organic layer is separated and evaporated to dryness. The residue is recrystallized from ethyl acetate to give the title compound.

In a similar manner when an appropriate amount of chloromethylpropionate, chloromethylacetate or chloromethylbutyrate is substituted for the chloromethylpivalate, the following respective products are obtained; 7-[[(1-pyrryl)acetyl]amino]-3-[[(1-methyltetrazol-5-yl) thio]methyl]-8-oxo-5-thia-1-azabicyclo[4.2.0]oct-2-ene-2-carboxylic acid propionyloxy methyl ester; 7[[(1-pyrryl)acetyl]amino]-3-[[(1-methyltetrazol-5-yl) thio]methyl]-8-oxo-5-thia-1-azabicyclo[4.2.0]oct-2-ene-2-carboxylic acid acetyloxymethyl ester; and 7[[(1-pyrryl) acetyl]amino]-3-[[(1-methyltetrazol-5-yl)thio]methyl]-8-oxo-5-thia-1-azabicyclo[4.2.0]oct-2-ene-2-carboxylic acid butyryloxymethyl ester.

EXAMPLE 8

7-[[(1-Pyrryl)acetyl]amino]-3-[[(1-methyltetrazol-5-yl)thio]methyl]-8-oxo-5-thia-1-azabicyclo[4.2.0]oct-2-ene-2-carboxylic acid N-butyrylaminomethyl ester To dimethylformamide is added the sodium salt of 7-[[(1-pyrryl)acetyl]amino]-3-[[(1-methyltetrazol-5-yl) thio]methyl]-8-oxo-5-thia-1-azabicyclo[4.2.0]-oct-2-ene-2-carboxylic acid, one equivalent, and an equivalent amount of N-butyrylaminomethyl chloride. The mixture is stirred at room temperature for about one hour after which it is carefully poured into ice water. The product precipitates and is recovered by filtration. The solid is dissolved in ethyl acetate and washed with aqueous sodium bicarbonate and then with water. The organic layer is dried over magnesium sulfate, filtered and evaporated to dryness in vacuo to give the title compound.

In a like manner ane when using the appropriate quantity of N-methyl-N-butyrylaminomethyl chloride or N-acetylaminomethyl chloride for N-butyrylaminoethyl chloride the following respective compounds are obtained; 7-[[(1-pyrryl)acetyl]amino]-3-[[(1-methyltetrazol-5-yl) thio]methyl]-8-oxo-5-thia-1-azabicyclo[4.2.0]oct-2-ene-2-carboxylic acid N-methyl-N-butyrylaminomethyl ester, 7-[[(1-pyrryl)acetyl]amino]-3-[[(1-methyltetrazol-5-yl) thio]methyl]-8-oxo-5-thia-1-azabicyclo[4.2.0]oct-2-ene-2 carboxylic acid N-acetyl aminomethyl ester.

EXAMPLE 9

7-[[(1-Pyrryl)acetyl]amino]-3-[[(1-methyltetrazol-5-yl)thio]methyl]-8-oxo-5-thia-1-azabicyclo4.2.0]oct-2-ene-2-carboxylic acid 2-amino-3-methylbutyryloxymethyl ester A suspension of 0.05 mole of 7-[[(1-pyrryl)acetyl-]amino-3-[[(1-methyltetrazol-5-yl)thio]methyl]-8-oxo-5-thia-1-azabicyclo[4.2.0]oct-2-ene-2-carboxylic acid sodium salt and 0.05 mole of N-tert-butokycarbonyl-L-valine chloromethyl ester, prepared by the procedure described in W. German Offen. No. 2,236,620 are mixed in 100 ml of dimethylformamide and stirred for about 72 hours. The mixture is diluted with ethyl acetate, washed with water, with aqueous sodium bicarbonate, and with water a second time. The organic layer is dried over magnesium sulfate, filtered and evaporated to give 7-[[(1-pyrryl)acetyl]methyl]-3-[[(1-methyltetrazol-5-yl)thio]methyl]-8-oxo-5-thia-1-azabicyclo[4.2.0]oct-2-ene-2-carboxylic N-tert-butoxycarbonyl-2-amino-3-methylbutyryloxy methyl ester from which the amine protecting group is removed by standard procedures to give the title compound as the product.

EXAMPLE 10

7-[[(1-Pyrryl)acetyl]amino]-3-[[(1-methyltetrazol-5-yl)thio]methyl]-8-oxo-5-thia-1-azabicyclo[4.2.0]oct-2-ene-2-carboxylic acid p-(acetyloxy)benzyl ester To a suspension of 6 mM of 7-[[(1-pyrryl)acetyl]amino]-3-[[(1-methyltetrazol-5-yl)thio]methyl]-8-oxo-5-thia-1-azabicyclo[4.2.0]oct-2-ene-2-carboxylic acid sodium salt in 40 ml of dimethylformamide (DMF) is added 2 equivalents of p-(acetyloxy)benxyl alcohol. The mixture is cooled to 0° C. after which 6.8mM of dicyclohexylcarbodiimide in 10 ml of DMF is added dropwise with stirring. The mixture is stirred at 0° C. for 1 hour and an additional 4 hours at room temperature. Dicyclohexylurea is removed by filtration. The filtrate is diluted with chloroform, washed with water, dried over magnesium sulfate, filtered and evaporated in vacuo to give the title compound.

When in the above procedure an appropriate amount of p-(propionyloxy)benzyl alcohol, p-(pivaloyloxy)benzyl alcohol or p-(butyryloxy)benzyl alcohol is substituted for p(acetyloxy)benzyl alcohol the following respective products are obtained.

7-[[(1-pyrryl)acetyl]amino]-3-[[(1-methyltetrazol-5-yl)thio]methyl]-8-oxo-5-thia-1-azabicyclo[4.2.0]oct-2-ene-2-carboxylic acid p-(propionyloxy)benzyl ester, 7-[[(1-pyrryl)acetyl]amino]-3-[[(1-methyltetrazol-5-yl)thio]methyl)-8-oxo-5-thia-1-azabicyclo[4.2.0]oct-2-ene-2-carboxylic acid p-(pivaloyloxy)benzyl ester, and 7-[[(1-pyrryl)acetyl]amino]-3-[[(1-methyltetrazol-5-yl)thio]methyl]-8-oxo-5-thia-1-azabicyclo[4.2.0]oct-2-ene-2-carboxylic acid p-(butyryloxy)benzyl ester.

EXAMPLE 11

7-[[(1-Pyrryl)acetyl]amino]-3-[[(1-methyltetrazol-5-yl)thio]methyl]-8-oxo-5-thia-1-azabicyclo[4.2.0]-oct-2-ene-2-carboxylic acid N-ethoxycarbonyl-N-methylaminonomethyl ester 7-[[(1-Pyrryl)acetyl]amino]-3-[[(1-methyltetrazol-5-yl)thio]methyl]-8-oxo-5-thia-1azabicyclo[4.2.0]oct-2-ene-2-carboxylic acid sodium slat, 3.0mM, in 60 ml of dimethylformamide is treated at room temperature with 3.0mM of N-chloromethyl-N-methylurethane for one hour. The mixture is carefully poured into ice water and the precipitated solid is removed by filtration and washed with water. The solid is dissolved in ethyl acetate and washed with aqueous sodium bicarbonate and then with water. The organic layer is dried over magnesium sulfate filtered and evaporated to dryness in vacuo to give the title compound.

EXAMPLE 12

7-[[(1-Pyrryl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid, tert-butyl ester (1-Pyrryl)acetic (0.03m) is added to water, the pH of which is adjusted to about 6.5 by the addition of sodium bicarbonate. This solution is cooled in an ice bath and to it is added 3-[[(5-methyl-1,3,4-thiadiazol-2-yl)thio]methyl]-7-amino-8-oxo-5-thia-1-azabicyclo[4.2.0]oct-2-ene-2-carboxylic acid tert-butyl ester (0.1m) (7-ATDCA) followed by N, N'-dicyclohexylcarbodiimide (0.01m) in cold dioxane. The mole ratio of (1-pyrryl) acetic acid/7-ATDCA/carbodiimide is 3/1/1. After standing overnight at ice bath temperature, the reaction mixture is filtered to remove solids. The filtrate is evaporated to dryness, the solids taken up in ethyl acetate, dried over magnesium sulfate and filtered. The ethyl acetate solution is concentrated and then treated with hexane. The title compound precipitates from solution, and is recovered.

EXAMPLE 13

7-[[(1-Pyrryl)acetyl]amino]-7-methoxy-3-(1-methyltetrazol-5-yl)thio]methyl-8-oxo-5-thia-1-azabicyclo[4.2.0]oct-2-ene-2-carboxylic acid (1-Pyrryl)acetic acid (0.09m) is added to water and the pH is adjusted to about 6.5 by the addition of sodium bicarbonate. This solution is cooled in a ice bath and to the solution is added 0.03m 7-amino-7-methoxy-3-[[(1-methyltetrazol-5-yl)thio]methyl]-8-oxo-5-thia-1-azabicyclo[4.2.0]oct-2-ene-2-carboxylic acid and 0.03m of dicyclohexylcarbodiimide in cold dioxane. After standing overnight at ice bath temperature, the reaction mixture is filtered to remove solids. The filtrate is evaporated to dryness, the solids taken up in ethyl acetate, dried over magnesium sulfate and filtered. The ethyl acetate solution is concentrated and then treated with hexane. The title compound precipitates from solution and is recovered.

We claim:

1. A compound of the formula

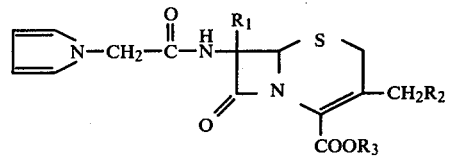

wherein $R_1$ is hydrogen or methoxy, $R_2$ is 1,3,4-thiadiazol-2-ylthio; 5-methyl-1,3,4-thiadiazol-2-ylthio; tetrazol-5-ylthio; 1-methyltetrazol-5-ylthio; 1,3,4-oxadiazol-2-ylthio; 5-methyl-1,3,4-oxadiazol-2-ylthio; 1,3,4-triazol-2-ylthio; 5-methyl-1,3,4-triazol-2-ylthio; 1,2,3-triazol-5-ylthio; $R_3$ is hydrogen, a cation of an alkali metal or an alkaline earth metal, ammonium or organic ammonium group selected from a lower alkyl ammonium or N-ethylpiperidinium group, a straight or branched alkyl group of from 1 to 4 carbon atoms, an alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched alkyl group of from 1 to 4 carbon atoms, a p(alkanoyloxy)benzyl group in which the alkanoyl moiety is straight or branched and has from 2 to 5 carbon atoms; an aminoalkanoyloxymethyl group in which the alkanoyl moiety has from 2 to 15 carbon atoms and the amino nitrogen may be mono- or di-substituted with a straight or branched lower alkyl group having from 1 to 4 carbon atoms or a pharmaceutically acceptable salt thereof.

2. A compound of claim 1 wherein $R_1$ is hydrogen, $R_2$ is 1-methyltetrazol-5-ylthio or 5-methyl-1,3,4-thiadiazol-2-ylthio; $R_3$ is hydrogen, a cation of an alkali metal or an alkaline earth metal, ammonium or organic ammonium cation selected from a lower alkyl ammonium or N-ethylpiperidinium group, straight or branched alkyl groups of from 1 to 4 carbon atoms, an alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched alkyl group having 1 to 4 carbon atoms; an alkoxycarbonylaminomethyl group in which the alkoxy moiety is straight or branched and has from 1 to 4 carbon atoms and the amine nitrogen may be substituted with or a straight or branched alkyl group of from 1 to 4 carbon atoms, p(alkanoyloxy)benzyl group in which the alkanoyl moiety is straight or branched and has from 2 to 5 carbon atoms; an aminoalkanoyloxymethyl group in which the alkanoyl moiety has from 2 to 15 carbon atoms and the amino nitrogen may be mono- or di-substituted with a straight or branched alkyl group having from 1 to 4 carbon atoms, or a pharmaceutically acceptable salt thereof.

3. A compound of claim 2 wherein $R_3$ is hydrogen or a pharmaceutically acceptable salt thereof.

4. A compound of claim 1 which is 7-[[(1-pyrryl)acetyl]amino]-3-[[(1-methyltetrazol-5-yl)thio]methyl]-8-oxo-5-thia-1-azabicyclo[4.2.0]oct-2-ene-2-carboxylic acid or a pharmaceutically acceptable salt thereof.

5. A compound of claim 1 which is 7-[[(1-pyrryl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid or a pharmaceutically acceptable salt thereof.

6. A compound of claim 1 which is 7-[[(1-pyrryl)acetyl]amino]-3-[[(1-methyltetrazol-5-yl)thio]methyl]-8-oxo-5-thia-1-azabicyclo[4.2.0]oct-2-ene-2-carboxylic acid pivaloyloxymethyl ester or a pharmaceutically acceptable salt thereof.

* * * * *